(12) United States Patent
van den Honert

(10) Patent No.: US 8,019,430 B2
(45) Date of Patent: Sep. 13, 2011

(54) STIMULATING AUDITORY NERVE FIBERS TO PROVIDE PITCH REPRESENTATION

(75) Inventor: Christopher van den Honert, Boulder, CO (US)

(73) Assignee: Cochlear Limited, Macquarie University, NSW ( * ) Notice: Subject to any disclaimer, the term of this patent is extended or adjusted under 35 U.S.C. 154(b) by 463 days.

(21) Appl. No.: 11/723,696

(22) Filed: Mar. 21, 2007

(65) Prior Publication Data
US 2008/0234783 A1 Sep. 25, 2008

(51) Int. Cl.
*A61N 1/00* (2006.01)
(52) U.S. Cl. ............................ 607/57; 607/56
(58) Field of Classification Search .................. 607/56, 607/57
See application file for complete search history.

(56) References Cited

U.S. PATENT DOCUMENTS

| | | | |
|---|---|---|---|
| 4,284,856 A | 8/1981 | Hochmair et al. | |
| 4,515,158 A | 5/1985 | Patrick et al. | |
| 4,593,696 A | 6/1986 | Hochmair et al. | |
| 4,813,417 A | 3/1989 | Soli et al. | |
| 4,823,795 A | 4/1989 | van den Honert | |
| 5,095,904 A | 3/1992 | Seligman et al. | |
| 5,531,774 A | 7/1996 | Schulman et al. | |
| 5,597,380 A | 1/1997 | McDermott et al. | |
| 5,776,172 A | 7/1998 | Schulman et al. | |
| 5,876,443 A | 3/1999 | Hochmair et al. | |
| 5,999,859 A | 12/1999 | Jolly | |
| 6,219,580 B1 * | 4/2001 | Faltys et al. ...................... | 607/57 |
| 6,272,382 B1 | 8/2001 | Faltys et al. | |
| 6,289,247 B1 | 9/2001 | Faltys et al. | |
| 6,321,125 B1 | 11/2001 | Kuzma | |
| 6,390,971 B1 | 5/2002 | Adams et al. | |
| 6,480,820 B1 * | 11/2002 | Clopton et al. ............... | 704/203 |
| 6,572,531 B2 | 6/2003 | Zilberman et al. | |
| 6,604,283 B1 | 8/2003 | Kuzma | |
| 6,611,717 B1 | 8/2003 | Clark et al. | |
| 6,732,073 B1 | 5/2004 | Kluender et al. | |
| 6,778,858 B1 | 8/2004 | Peeters | |
| 6,915,166 B1 | 7/2005 | Stecker et al. | |
| 6,920,360 B2 | 7/2005 | Lee et al. | |
| 7,082,332 B2 | 7/2006 | Blamey et al. | |

(Continued)

FOREIGN PATENT DOCUMENTS

AU 2001265692 9/2004

(Continued)

OTHER PUBLICATIONS

Robles, et al., "Mechanics of the Mammalian Cochlea," *Physiological Review*, Jul. 3, 2001, pp. 1305-1352, vol. 81, No. 3, U.S.A.

(Continued)

*Primary Examiner* — Niketa I Patel
*Assistant Examiner* — Catherine Voorhees
(74) *Attorney, Agent, or Firm* — Kilpatrick Townsend & Stockton LLP

(57) ABSTRACT

Aspects provide methods and sound processor for encoding stimulation signals to convey pitch perception information to a recipient. The method may comprise identifying a first stimulation site based on a selected frequency component of the sound signal that contains pitch perception information, wherein a stimulation signal is generated based on the selected frequency component; determining a second stimulation site adjacent to the first stimulation site; and determining a time delay between when the second stimulation site is independently stimulated with the stimulation signal and when the first stimulation site is independently stimulated with the stimulation signal.

23 Claims, 7 Drawing Sheets

U.S. PATENT DOCUMENTS

| | | | |
|---|---|---|---|
| 7,103,417 B1* | 9/2006 | Segel et al. | 607/57 |
| 7,251,530 B1 | 7/2007 | Overstreet et al. | |
| 7,292,892 B2 | 11/2007 | Litvak et al. | |
| 7,729,775 B1* | 6/2010 | Saoji et al. | 607/57 |
| 2003/0135247 A1 | 7/2003 | Zierhofer | |
| 2003/0171786 A1 | 9/2003 | Blamey et al. | |
| 2004/0015210 A1 | 1/2004 | Clark et al. | |
| 2004/0136556 A1 | 7/2004 | Litvak et al. | |
| 2005/0010267 A1 | 1/2005 | Ibrahim | |
| 2005/0177205 A1 | 8/2005 | Kwon et al. | |
| 2005/0187592 A1 | 8/2005 | Seligman et al. | |
| 2005/0192646 A1* | 9/2005 | Grayden et al. | 607/57 |
| 2006/0080087 A1* | 4/2006 | Vandali et al. | 704/207 |
| 2006/0212095 A1* | 9/2006 | Wolfe et al. | 607/57 |
| 2006/0265061 A1 | 11/2006 | Kwon et al. | |

FOREIGN PATENT DOCUMENTS

| | | |
|---|---|---|
| EP | 0661905 | 7/1995 |
| WO | 0199470 | 12/2001 |
| WO | 2004021363 | 3/2004 |
| WO | 2005057983 | 6/2005 |

OTHER PUBLICATIONS

International Search Report. PCT/US2008/057690. Mailed Aug. 29, 2008.

International Searching Authority, "Written Opinion," issued in connection with International Patent Application No. PCT/US2008/057690, mailed on Aug. 29, 2008 (5 pages).

International Preliminary Examining Authority, "International Preliminary Report on Patentability," issued in connection with International Patent Application No. PCT/US2008/057690, on Feb. 27, 2009 (7 pages).

European Search Report, "Extended European Search Report," issued in connection with European Patent Application No. 08744124.2, on May 20, 2010 (6 pages).

U.S. Appl. No. 11/030,980, Office Action mailed on Aug. 27, 2009, 11 Pages.

U.S. Appl. No. 11/030,980, Office Action mailed on Apr. 14, 2010, 15 Pages.

U.S. Appl. No. 11/030,980, Office Action mailed on Jul. 19, 2010, 19 Pages.

U.S. Appl. No. 11/030,980, Office Action mailed on Mar. 25, 2008, 8 Pages.

U.S. Appl. No. 11/030,980, Office Action mailed on Dec. 19, 2008, 9 Pages.

U.S. Appl. No. 11/335,563, Office Action mailed on Jul. 17, 2008, 11 Pages.

U.S. Appl. No. 11/335,563, Office Action mailed on Mar. 9, 2010, 12 Pages.

U.S. Appl. No. 11/030,980, Office Action mailed on Jan. 20, 2011 15 Pages.

U.S. Appl. No. 11/335,563, Office Action mailed on Oct. 15, 2010, 16 Pages.

U.S. Appl. No. 11/335,563, Office Action mailed on Jul. 20, 2009, 7 Pages.

U.S. Appl. No. 11/335,563, Office Action mailed on Jan. 23, 2009, 8 Pages.

Australian Application No. 2005200067, Office Action mailed on Apr. 3, 2009.

* cited by examiner

STIMULATING AUDITORY NERVE FIBERS TO PROVIDE PITCH REPRESENTATION

BACKGROUND

1. Field of the Invention

The present invention relates generally to prosthetic hearing implants, and more particularly, to stimulating auditory nerve fibers to provide pitch representation in a prosthetic hearing implant.

2. Related Art

Sensorineural hearing loss is due to the absence or destruction of the hair cells in the cochlea that are needed to transduce acoustic signals into auditory nerve impulses. Individuals suffering from a severe or profound form of this type of hearing loss are unable to derive benefit from hearing aids. This is because the natural mechanisms for transducing sound energy into auditory nerve impulses have been damaged. In such cases, prosthetic hearing implants, such as COCHLEAR™ and NUCLEUS® implants produced by COCHLEAR LIMITED of Australia, have been developed to provide the sensation of hearing to such individuals. In these kind of prosthetic hearing implants, electrical stimulation is provided via stimulating electrodes positioned as close as possible to the nerve fibers of the auditory nerve, essentially bypassing the hair cells in the cochlea. The application of a stimulation pattern to the nerve endings causes impulses to be sent to the brain via the auditory nerve, resulting in the brain perceiving the impulses as sound.

Despite considerable practical success with prosthetic hearing implants, there are significant shortcomings in conveying all the aspects of sound to a recipient using existing implants and techniques. One shortcoming is the deficiency in representing pitch, such as "complex" or musical pitch. Pitch is a perceptual attribute of sound that allows the sound to be ranked on a low-to-high scale. In general, sounds producing well-defined musical pitch are those whose acoustic pressure waveforms repeat periodically. The pitch of the sound is determined by the repetition rate of the waveform, referred to as the "fundamental frequency." Pitch can be defined with or without reference to music. Perception of musical pitch is of great importance, even for non-musical sounds. For example, voice pitch is a cue commonly used by natural hearing listeners to segregate and attend to one speaker among competing background speakers. Voice pitch is also important for conveying semantic information in tonal languages. For music and non-musical sound, it is important to note that pitch is an attribute of a percept, not a property of an electrical stimulus or sound.

SUMMARY

According to one aspect of the present invention, there is provided a method for representing a sound signal for a prosthetic hearing implant comprising: identifying a first stimulation site based on a selected frequency component of the sound signal that contains pitch perception information; determining a second stimulation site adjacent to the first stimulation site; generating a stimulation signal based on the selected frequency component; and determining a time delay between when the second stimulation site is independently stimulated with the stimulation signal and when the first stimulation site is independently stimulated with the stimulation signal.

According to a second broad aspect of the present invention, there is provided a sound processor for a prosthetic hearing implant comprising: a plurality of filters that each produce an output from a sound signal; frequency selecting means for selecting the output from a selected filter of the plurality filters and another filter of the plurality of filters, wherein the another filter is adjacent to the selected filter; and timing delay generator configured to determine a time delay the separates a first stimulation signal from the another filter and a second stimulation signal from the selected filter.

BRIEF DESCRIPTION OF THE DRAWINGS

Embodiments of the present invention will be described in conjunction with the accompanying drawings, in which.

DETAILED DESCRIPTION

Figure 1:
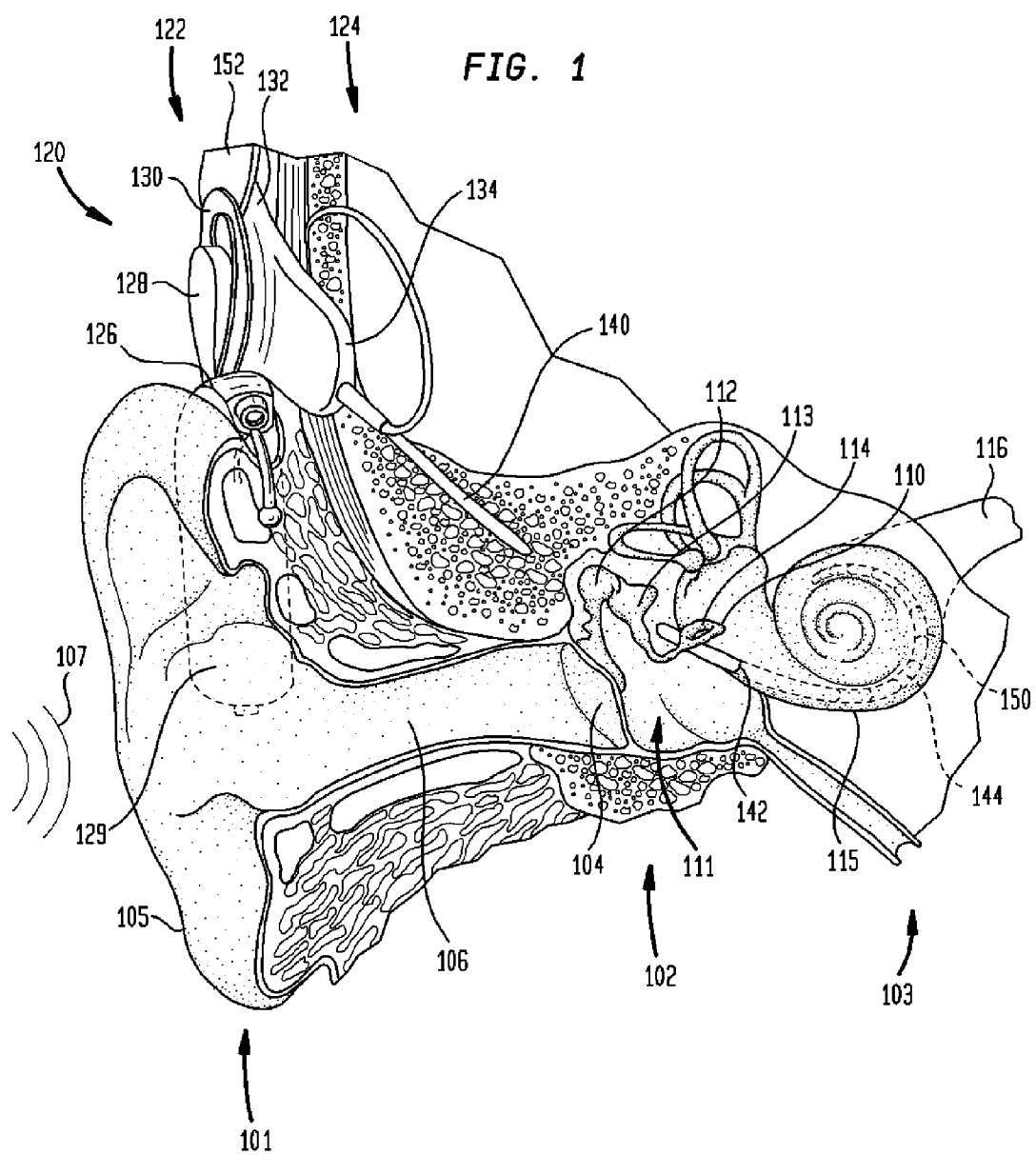
FIG. 1 is a schematic diagram of an exemplary prosthetic hearing implant with which aspects of the present invention may be implemented.

Aspects of the present invention are generally directed to a prosthetic hearing implant in which the pitch of a received sound is conveyed to the recipient along with stimulation signal(s) representing the received sound. Generally, stimulation signals are generated by a sound processor to be applied to adjacent or neighboring auditory nerve fiber populations via adjacent stimulating electrodes. The nerve fiber populations, referred to as stimulation sites or locations within the cochlea, are discrete and adjacent. The sound processor selects a first stimulation site corresponding to a frequency component of the received sound determined to contain pitch perception information. An adjacent stimulation site may be more basal than the selected first stimulation site, although in some embodiments the adjacent stimulation site may be more apical than the selected first stimulation site. The timing difference between the stimulation signals independently applied to the first and second stimulation sites is determined so as to attain a combined effect that conveys pitch to the recipient.

Unlike conventional stimulation in which stimulation sites are chosen based on the frequency components of the received sound, embodiments of the present invention select adjacent stimulation sites for conveying pitch perception information. Each of these stimulation sites will receive stimulation signals separated by a time instant. Preferably, the stimulation at each stimulation site is focused so that the stimulation is independent, i.e. does not recruit nerve fibers of adjacent stimulation sites.

In one embodiment, the stimulation signals are repeatedly applied to each of the selected adjacent stimulation sites. This embodiment of the invention is based on replicating the normal auditory filters exhibited by the basilar membrane, which gives rise to the phase delays among auditory nerve fibers. Such embodiments of the present invention allow a recipient to recognize pitch by providing repeating stimulation at two adjacent stimulation sites in the cochlea. Such stimulation is independently focused to each particular stimulation site. Increased recognition of pitch using the conveyed pitch perception information allows a recipient to enjoy music and identify cues from vocal pitches, which is critical in tonal languages.

To convey pitch perception information, embodiments of the present invention use existing pitch theories to determine which frequency components to select for stimulation. In existing pitch perception stimulation techniques, two theories—"pitch" and "rate," and their variants—have been advanced to account for how the central nervous system (CNS) extracts pitch information from discharges of the auditory nerve fibers. These theories derive from two cochlea function attributes. The first attribute is basilar membrane tuning. Each "place" along the basilar membrane is most sensitive to sound energy at a particular frequency, varying systematically from about 20 kHz at the base to about 20 Hz at the apex. According to this attribute, the CNS could use differences among discharge patterns at different places to infer where the harmonics of a sound are, or more generally, where most of the energy is in the sound spectrum. This is the basis of the "place" theory of pitch, according to which pitch is determined from spatial analysis of auditory nerve activity. The second attribute is auditory nerve phase locking. In response to a periodic sound an auditory nerve fiber tends to discharge spikes at a rate equal to the fundamental or the harmonic to which it is most closely tuned. This is the basis of the "rate" theory of pitch, where the CNS determines pitch based on the timing of neural spikes.

The theories that combined both spatial and temporal information from auditory nerve discharges have been most successful in explaining observed pitch phenomena in normal hearing. For sounds with resolved harmonics that provide the strongest pitch percept, it seems the CNS uses both a temporal analysis and an associated spatial analysis to identify the harmonics of a periodic sound and determine their spacing. However, these existing theories are not yet able to account entirely for all observed pitch phenomena. The place theory has traditionally invoked nerve discharge rate as the "metric" that the CNS might monitor to infer acoustic energy in the input spectrum. But rate versus place profiles are very broad at medium and high sound intensities, essentially having no spatial profile and thus cannot provide pitch perception information. Also, at high intensities a neuron's "best frequency" shifts downward, but perceived pitch does not change. In contrast, the temporal patterning of a neuron's discharge is largely independent of intensity.

A weakness of the rate theory is that periodic sounds having harmonics which all fall within one auditory filter bandwidth (so-called unresolved harmonics) produce only a weak pitch percept that is discernable only up to about 600 Hz. Such sounds produce nerve discharges at the fundamental rate among responding neurons, but do not provide any information about harmonic spacing. Thus, prior techniques that rely solely on rate theory fail to convey pitch perception information to recipients.

Several other alternatives have been advanced to describe the temporal and spatial codes from which the CNS may extract pitch information. Temporal analyzers generally fall into two classes: those that depend upon some absolute time calibration of the neural circuitry, e.g. autocorrelators, and those that perform a differential analysis of timing among neighboring neurons with differing best frequencies, e.g. coincidence detectors. The second class of temporal analyzers is more attractive from a teleological perspective because such analyzers do not require neural circuits with absolute (and sometimes large) time delays as would an autocorrelator. An alternative method is described as a traveling wave based on a basilar motion wave described in U.S. Pat. No. 7,082, 332, entitled, "Sound Processor for Cochlear Implant," issued on Jul. 25, 2006, which is hereby incorporated by reference herein.

Another approach to determine pitch perception is neural phase response. Discharges of an auditory nerve fiber are similar to the output of a filter responding to the acoustic input signal. The magnitude and phase of the filter's transfer function can be measured from neural spike rate and timing respectively in response to steady state sinusoidal inputs, e.g. Fourier transform of the nerve fiber's "cycle histogram".

The magnitude response of each filter transfer function exhibits tuning, i.e. maximal response at a single frequency. Tuning is sharpest for high frequency neurons, and least sharp for low frequency neurons. Generally the high-cut skirt of the filter is substantially steeper than the low-cut skirt. The phase response is relatively flat below the center frequency (CF), and exhibits a steep drop as frequency crosses CF. This steep phase shift is a familiar attribute of a sharply resonant minimum-phase linear filter. The steep drop in the phase response results in a sudden drop in propagation velocity of the traveling wave as it passes the resonant point of the basilar membrane.

These localized phase discontinuities provide an attractive encoding mechanism by which the CNS may identify existence of harmonics in the original audio signal using simple coincidence detection networks perhaps with fixed small delay lines. Prior research proposed that phase discontinuities across fibers of differing CF might be used by the CNS to infer pitch on the Medial Superior Olive and other locations in the brainstem. Embodiments of the present invention use localized phase discontinues of neural phase response when selecting frequency components that contain pitch perception information for the recipient's overall sound recognition.

The present invention will now be described in terms of implants and devices that may be used to implement embodiments of the present invention. FIG. 1 is a perspective view of an exemplary prosthetic hearing implant 120 in which embodiments of the present invention may be advantageously implemented. In fully functional human hearing anatomy, outer ear 101 comprises an auricle 105 and an ear canal 106. A sound signal or acoustic pressure wave 107 is collected by auricle 105 and channeled into and through ear canal 106. Disposed across the distal end of ear canal 106 is a tympanic membrane 104 which vibrates in response to acoustic wave 107. This vibration is coupled to oval window, or fenestra ovalis, 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115.

Such fluid motion, in turn, activates tiny hair cells (not shown) that line the inside of cochlea 115 through the motion of the basilar membrane (not shown). The basilar membrane is a vibrating structure in the inner ear whose resonant frequency varies systematically. At the basal end where the basilar membrane is narrow and taught, the membrane vibrates in response to high frequencies, approximately 20 kHz in humans. While at the apical end, where the basilar membrane is wide and slack, the membrane vibrates in response to low frequencies, approximately 20 Hz in humans. At any point along the basilar membrane, the membrane behaves like a sharply tuned bandpass filter with a magnitude response that is maximum a particular frequency, and a phase response that exhibits a sharp increase in phase delay at the frequency of resonance. Both magnitude and phase responses of the filter behavior are reflected in the discharges of the auditory nerve fibers innervating hair cells at the corresponding place. Magnitude is reflected in the average discharge rate of those nerve fibers. The nerves also exhibit phase locking, whereby they tend to discharge impulses at a particular point in the sinusoidal cycle of the basilar membrane vibration. The point in the cycle at which the nerves fire varies with frequency, reflecting the phase response of the filter behavior of the basilar membrane.

Activation of the hair cells causes appropriate nerve impulses to be transferred through the spiral ganglion cells and auditory nerve 116 to the central nervous system (CNS), which perceives sound and pitch. In deaf persons, there is an absence or destruction of the hair cells. A prosthetic hearing implant 120 is utilized to directly stimulate the ganglion cells to provide a hearing sensation to the recipient.

FIG. 1 also shows how a prosthetic hearing implant 120 is positioned in relation to outer ear 101, middle ear 102 and inner ear 103. Prosthetic hearing implant 120 comprises external component assembly 122 which is directly or indirectly attached to the body of the recipient, and an internal component assembly 124 which is temporarily or permanently implanted in the recipient. External assembly 122 comprises several components including a plurality of audio sensors, such as sound transducers or microphones, spatially arranged on external components 122 of prosthetic hearing implant 120 for detecting sound.

Sound processor 126 is configured to generate coded stimulation control signals representing sound detected by the plurality of audio sensors. These coded signals are then provided to an external transmitter unit 128. In the embodiment shown in FIG. 1, sound processor 126 is a behind the ear (BTE) sound processing unit. The BTE is constructed and arranged so that it can fit behind the outer ear 101 of a recipient. BTE may include a power source 129 to power all elements of prosthetic hearing implant 120, such as the external coil 130. Power source 129 may be a battery, such as a zinc-air battery or other suitable secondary batteries. In certain embodiments, power source 129 may be physically disconnected from the BTE, thereby causing the BTE to discontinue operation. Furthermore, in other embodiments, accessories can be connected to the BTE to add additional functionality. Note that in some prosthetic hearing implants 120, which are totally implantable, the sound processor 126 may be located with internal component assembly 124 and have a power link to an external power source 129.

It would be appreciated by one of ordinary skill in the art that sound processor 126 may also comprise a body-worn sound processor, a modular sound processor or a sound processor headset. Details of the sound processing performed in sound processor 126 in accordance with embodiments of the present invention are discussed below.

External transmitter unit 128 comprises an external coil 130 and, preferably, a magnet (not shown) secured directly or indirectly in external coil 130. External transmitter unit 128 is configured to transmit the coded signals from sound processor 126, along with power from a power source 129 such as a battery to internal components 124 through tissue 152.

Internal components 124 comprise an internal receiver unit 132 having an internal coil (not shown) that receives and transmits power and coded signals received from external assembly 122 to a stimulator unit 134 to apply the coded signal to cochlea 115 via an implanted electrode assembly 140. Electrode assembly 140 enters cochlea 115 at cochleostomy region 142 and has one or more electrodes 150 positioned to be substantially aligned with stimulation sites in the tonotopically-mapped cochlea 115. Signals generated by stimulator unit 134 are typically applied by an array 144 of electrodes 150 to cochlea 115, thereby stimulating auditory nerves 116. In some embodiments the electrodes 150 may be micro-electrodes.

Alternatively, electrodes 150 may include one or more microscopic electrodes configured to stimulate a relatively small, discrete or localized stimulation site in the cochlea. A stimulation site comprises a neighboring population of nerve fibers. Microscopic electrodes may also be use to stimulate parts of the auditory system other than the cochlea. For example, microscopic electrodes may stimulate the cochlear nucleus, inferior colliculus, or auditory cortex or other places within the central nervous system (CNS). Also, any stimulation focusing or sharpening techniques may also be employed to focus the stimulation to a discrete stimulation site, such as the technique described in US Publication No. 2006/0247735, entitled "Focused Stimulation in a Medical Stimulation Device," the entire contents and disclosure of which is hereby incorporated by reference. These electrodes and stimulation sharpening techniques limit the stimulation that might spread across neighboring stimulation site. The spreading function recruits several nerve population thereby creating broad stimulation of multiple stimulation sites.

Figure 2:
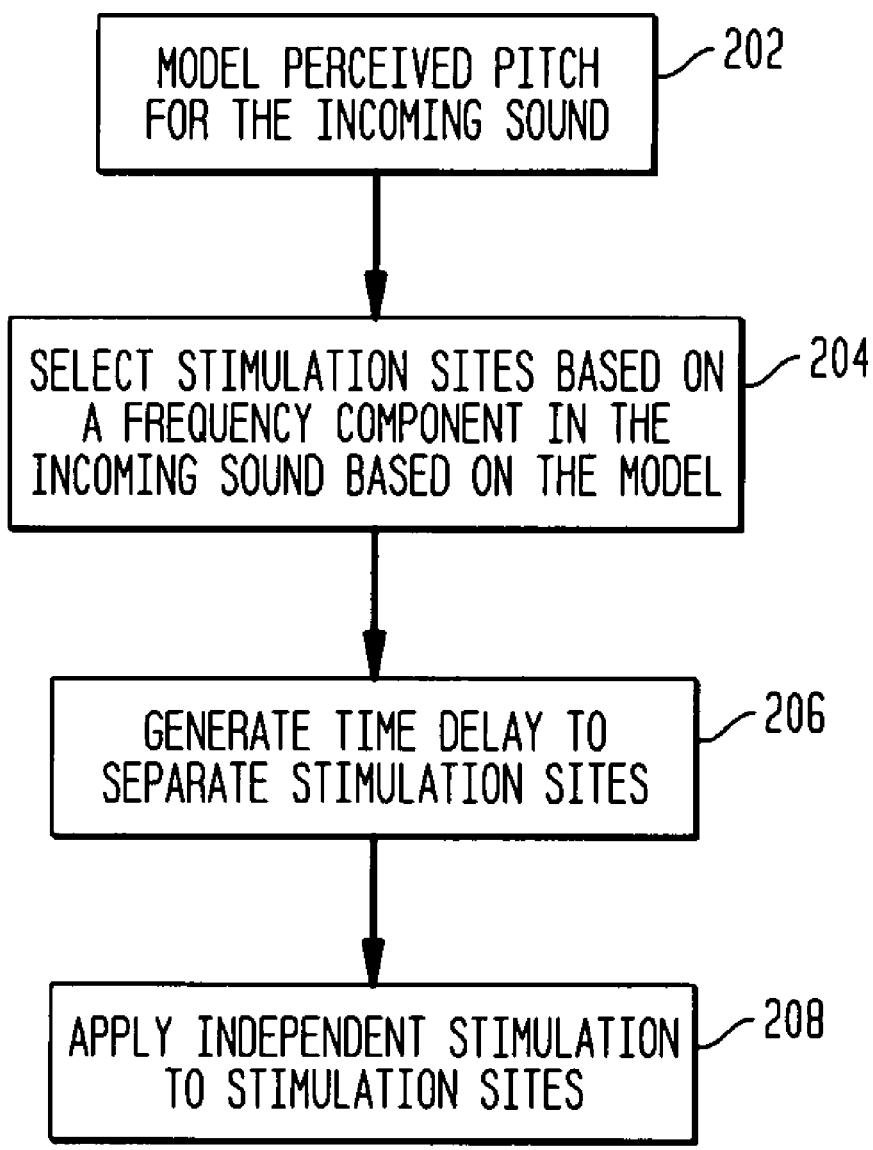
FIG. 2 is a flowchart of overall method of selecting adjacent stimulation sites according to embodiments of the present invention.

FIG. 2 is a flow chart of a method for generating stimulation signals in accordance with one embodiment of the present invention. In process 200 a time instant or delay between the stimulation signals is set using, for example, sound processor 126, and then stimulating selected electrodes 150. First, pitch perception information from an incoming sound signal is determined at block 202. This may be done based on a normal hearing model. At block 204, the incoming sound signal is analyzed to identify which frequency components likely containing pitch information. This analysis and identification may be performed, for example, using a filterbank or FFT. For each such frequency component, an appropriate stimulation site within cochlea 115 is identified, as well as second stimulation site that is basal and adjacent to the selected stimulation site.

At block 206, a time delay is determined to temporarily separate application of each of the two stimulation signals, where the most basal stimulation site is stimulated first. In embodiments using a filterbank, each certain stimulation site in the cochlea will have a corresponding filter based on a corresponding frequency range. These two stimulation sites may be stimulated with two adjacent electrodes 150. In one embodiment, during stimulation at block 208, the frequency component to be represented is stimulated at the most basal stimulation site alone such that recruitment of the most apical stimulation site does not occur. After some time delay the most apical stimulation site is stimulated independently so as to create a phase delay between nerve impulses emanating from those two stimulation sites. Various embodiments may stimulation each stimulation site with a stimulation signal of the selected frequency components. The order of stimulation may be reversed in some embodiments such that the more apical stimulation site is stimulated first. This process may be repeated as necessary to convey pitch perception information to the recipient.

Figure 3:
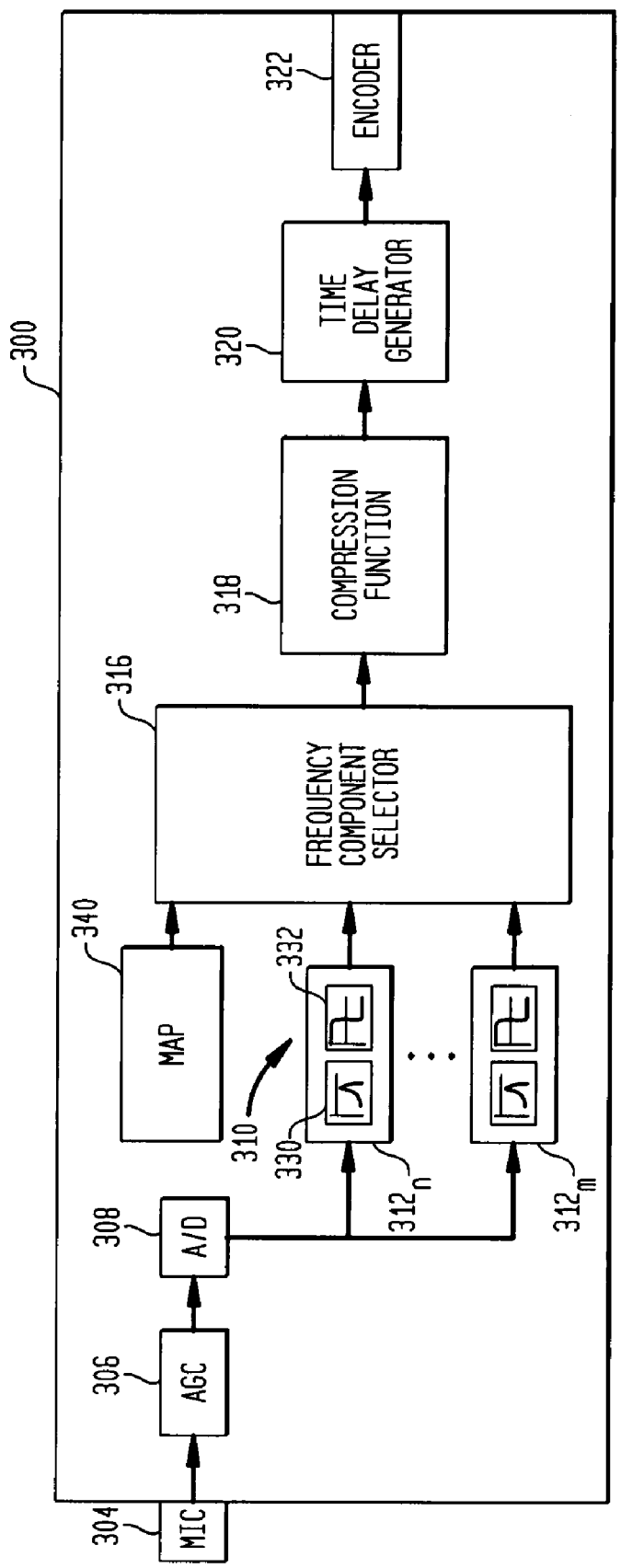
FIG. 3 is a functional block diagram of an embodiment a sound processor in which aspects of the present invention may be implemented.

FIG. 3 is a block diagram of one embodiment of sound processor 126, referred to herein as sound processor 300. Sound processor 300 comprises an acoustic gain control (AGC) 306, A/D converter 308, filterbank 310 having a plurality of band pass filters 312, frequency component selector 316, compression function 318, time delay generator 320 and encoder 322. It should be readily apparent to one of ordinary skill in the art that additional or alternative conventional components may also be incorporated in sound processor 300, such as envelope detectors (rectification/low-pass filtering). Microphone 304 converts a received sound signal to an electrical signal. AGC 306 is a sensitivity control to adjust the attenuation of the received electrical signal from microphone 304. A/D converter 308 produces a digital output of the electrical signal representative of the sound signal. Each band pass filter 312 corresponds to the frequency of a tonotopically-placed electrode 150 inside cochlea 115. Each filter 312 may pass through a frequency band having a different center frequency. Also each band pass filter 312 identifies an amplitude component 330 and phase component 332 of the sound signal received by microphone 304. Frequency component selector 316 uses a recipient's MAP 340 to adjust for the particular recipient the signals from band pass filters 312. MAP 340 may be stored in any memory device now or later developed. Encoder 322 transmits the stimulation signals and time instants to implanted stimulator/receiver unit 134 that generates corresponding stimulation signals for the selected electrodes 150. A digital-signal-processor or microprocessor may perform one or more functions of sound processor 300.

Frequency component selector 316 identifies the band pass filter $312_n$ having a frequency component desired for pitch representation to the recipient, and an adjacent band pass filter $312_m$. Both the selected band pass filter $312_n$ and adjacent band pass filter $312_m$ are used to generate the stimulation pulses using compression function 318. Time delay generator 320 determines the time delay between stimulating an electrode with a corresponding stimulation signal from selected band pass filter $312_n$ and stimulating an adjacent electrode with a corresponding stimulation signal from adjacent band pass filter $312_m$.

In some embodiments the plurality of filters may comprise minimum-phase linear filters whose magnitude response approximates that of the human auditory filter will likely have a phase response that is also approximately correct. Use of such filters is described in U.S. Pat. No. 4,813,417, entitled "Signal Processor for and an Auditory Prosthesis Utilizing Channel Dominance," to Soli, et al. and van den Honert, C. "Reproducing auditory nerve temporal patterns with sharply resonant filters," in *Cochlear Implants*, J. M. Miller and F. A. Spelman, eds., Springer Verlag, (1990) pp. 115-131, the entire contents and disclosure of which is hereby incorporated by reference. Alternatively, the filters may be created with phase responses explicitly designed to model known psychophysical data, which is described in Oxenham, A. J., and Dau, T., "Reconciling frequency selectivity and phase effects in masking," J. Acoust. Soc. Am., 110:1525-1538 (2001), the entire contents and disclosure of which is hereby incorporated by reference.

Figure 4:
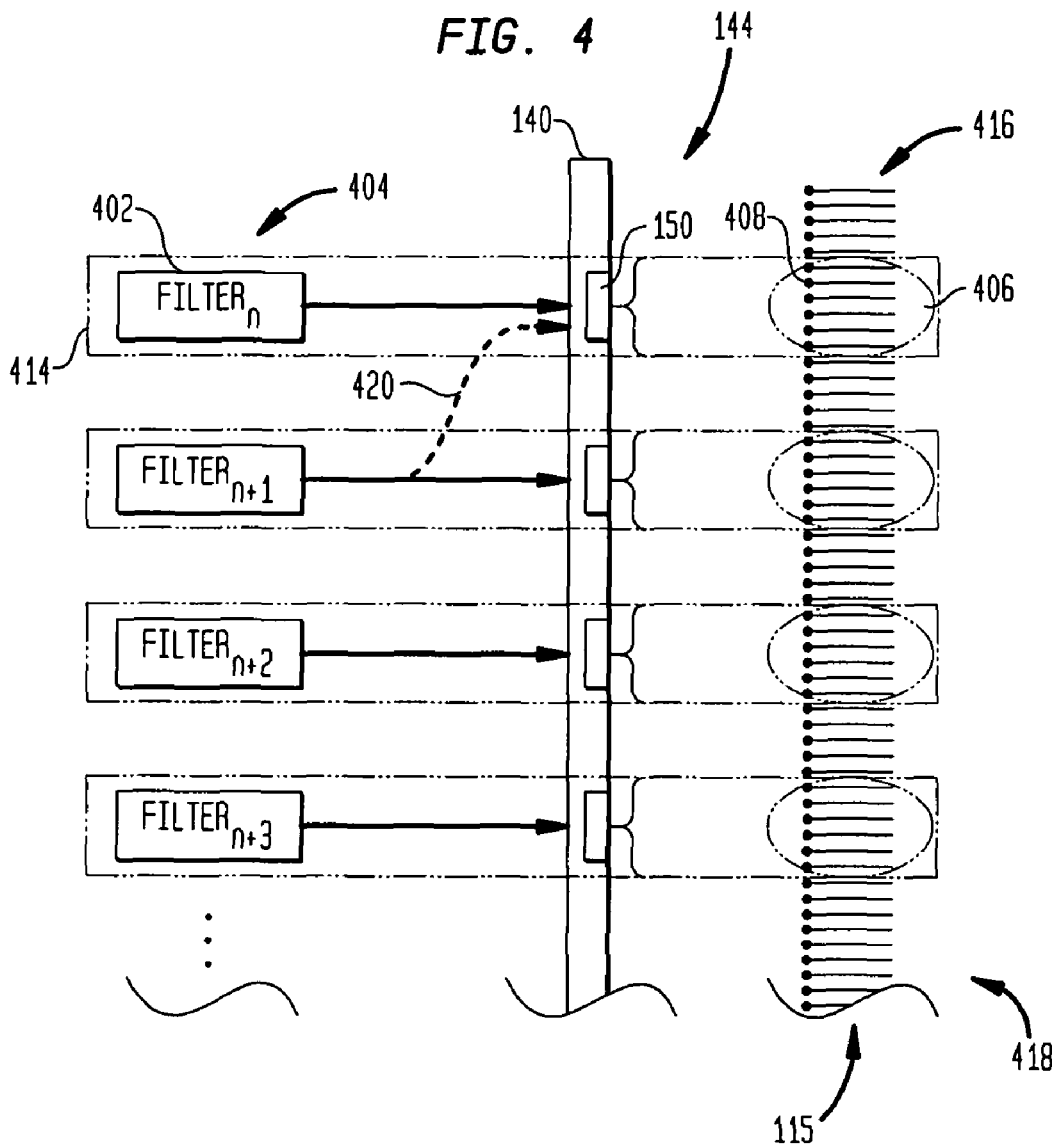
FIG. 4 is a functional block diagram showing the various components of a frequency channel.

Each of the plurality of filters 402 (collectively referred to as a filterbank 404) covers a center frequency corresponding to the frequency range of a stimulation site 406 in the tonotopically-arranged cochlea 115 as shown in FIG. 4. A stimulation site 406 comprises a plurality of adjacent nerve populations 408. In one embodiment, one electrode 150 on an array of electrodes 144 disposed on a carrier member 140 is provided for each stimulation site 406. Filter 402, electrode 410 and stimulation site 406 together form a channel 414. Each channel 414 covers the different frequency range from basal end 416 to apical end 418 of cochlea 115. Thus, when referring to adjacent channels 414 it is understood to also refer to adjacent filters 402 and the corresponding adjacent stimulation sites 406 for each filter 402. For example, if 22 stimulation sites are available, 22 filters 402 may be included in the filterbank 404. Note that in FIG. 4, each electrode 150 discretely stimulates a stimulation site such that there is minimal, and preferably no, recruitment of adjacent stimulation sites. A higher density electrode array, smaller electrodes, or a stimulation focusing or sharpening technique, may be implemented in alternative embodiments of the invention to increase the number of available stimulation sites 406, thereby increasing the number of filters 402.

For normal stimulation the output of a filter 402 in a channel 414 is converted to a stimulation signal for the stimulation in the channel 414. In some embodiments, the adjacent channel 414 that is selected may apply the filter output of its own channel or may apply the filter output of the selected channel, as shown by arrow 420. Thus, the same output from the selected channel 414 is repeatedly stimulated at two adjacent stimulation sites 406 in cochlea 115. In other embodiments, the output of the adjacent channel 414 is applied to its stimulation site 406, regardless of the frequency or amount of energy in the channel.

Figure 5:
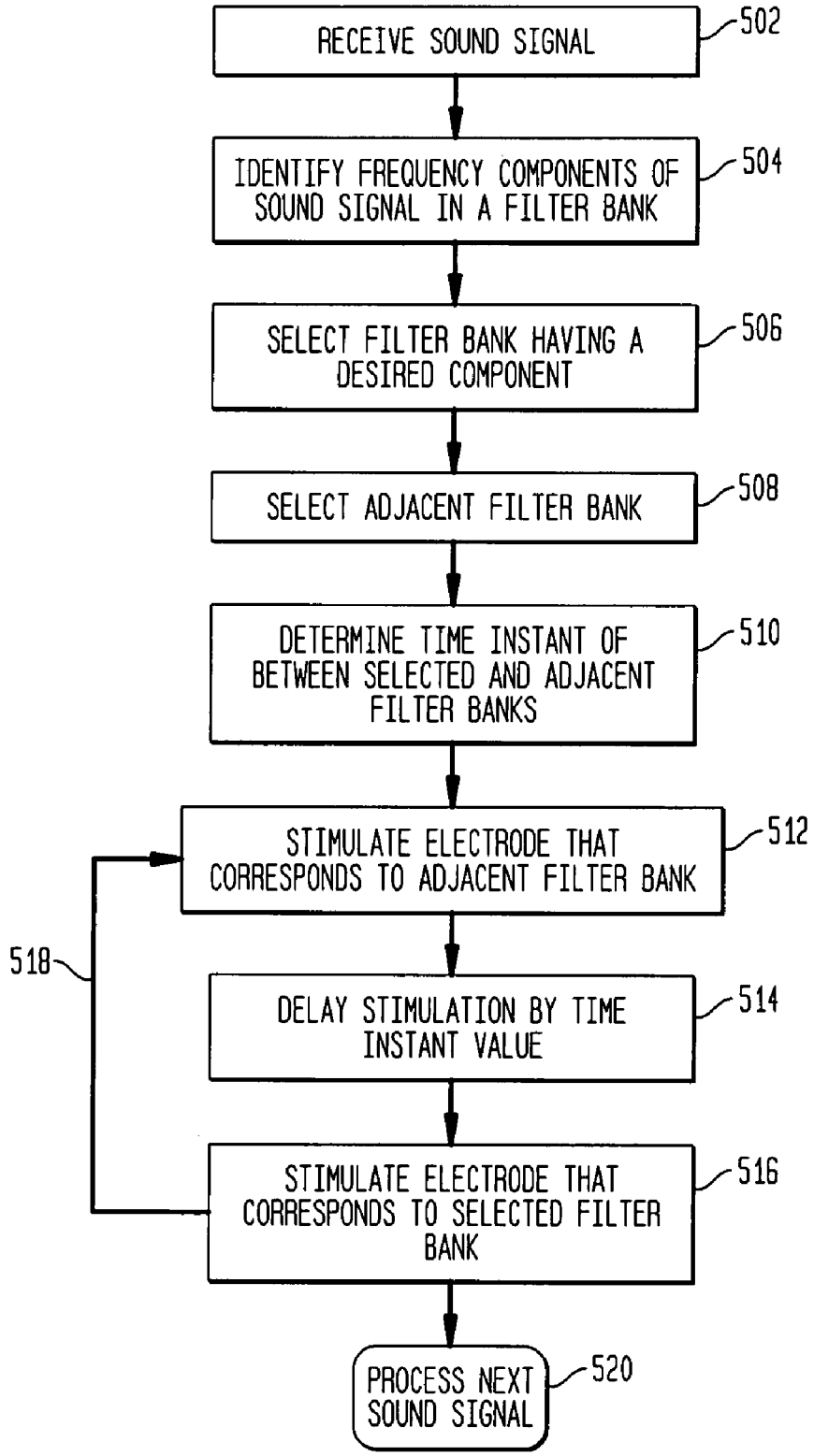
FIG. 5 is a flowchart of a method according to embodiments of the present invention.

FIG. 5 is a flowchart illustrating one exemplary method of the present invention for representing pitch using electric stimuli for a sensorineural deficient recipient. The process 500 begins upon receipt of a sound signal at block 502. The sound signal may be a vocal sound, musical sound, or other environmental sound. The sound signal may be optionally pre-processed using AGCs, amplifiers, A/D converters and converted into an electrical audio input signal representative of the sound signal. Next, at block 504, the electrical signal is separated into frequency components using, for example, a bank of filters. Each filter produces an output that may be further processed using an envelop detector and are sent to a selector.

The selector implements a strategy in block 506 to determine which frequency components should be represented to recipient. Note that multiple frequency components from different filters may be selected in some embodiments. Some strategies may select based on which filter has the largest magnitude. Also, other strategies may select based on which filter exhibits a localized phase discontinuity that approximates a tone frequency determined from a normal hearing perception model. Alternatively, the sound signal may be analyzed to identify any contained harmonic complexes, and only components from selected harmonic complexes may be represented. For example, a sound signal might contain harmonics of 100 Hz (100, 200, 500, etc.) and harmonics of 250 Hz (250, 500, 750, etc.) and harmonics of 512 Hz (412, 824, 1648, etc.). Given a limited number of available stimulation sites (electrodes), it may not be possible to represent all of those components. So the strategy may choose only the harmonics of 100 Hz or only the harmonics of 250 Hz for presentation to produce a strong corresponding pitch sensation for the recipient.

The selection may be also be determined by reference to a recipient's MAP. Also, in cases where the filter's center frequency exceeds the maximum sustainable discharge rate for a neuron, a model of neural refractoriness or some other means of selectively omitting stimuli may be implemented.

Once the frequency component is selected from one of the filters, an adjacent filter is also selected at block 508. In some embodiments, the frequency component of that filter may also be used in the stimulation regardless of magnitude, phase or harmonics. In other embodiments the adjacent stimulation site is selected by reference to the filters, and the frequency component of the selected filter is used to generate a stimulation signal for both the selected and adjacent stimulation sites. In some embodiments, the adjacent filter corresponds to a stimulation site that is basal or at a higher frequency that the selected filter.

Once the two filters corresponding to two adjacent stimulation sites in the cochlea are selected, a time instant or delay is determined in block 510. The outputs of each filter are converted to a pulse using a compression function or pulse generator. The pulse is part of a stimulation signal for convey sound information to the recipient of the implant. The time instant is a delay signal that separates the stimulation or application of each stimulation signal using the electrodes. For any given stimulation site in the cochlea, any time delay that exceeds some minimum value of approximately 0.1 ms may be sufficient. Such a time delay separates stimulation and the CNS may perceive nerve impulses that are not coincident with nerve impulses from a neighboring stimulation site. An acceptable time delay may be one that is long enough such that the two stimulation signals are not deemed simultaneous by the CNS. The required time delay may vary depending on the stimulation site that corresponds to the selected filter. Shorter time delays of approximately 600 µsec may be sufficient at the basal end where high frequencies are represented, whereas long delays of approximately 5 ms may be necessary at the apical end where low frequencies are represented.

Time delays may be determined using several different techniques. In one embodiment, the output of each filter 402 is used to determine the time at which stimulation is to be applied at the stimulation site 406 within cochlea 115 to produce proper relative timing among nerve fibers from differing points on the basilar membrane. For example, each positive peak or zero crossing in the filter outputs could define such time delays.

The time delays and stimulation signals are encoded and sent to the corresponding electrodes for stimulation. Each of these signals may be sent as a group or individually. In block 512 the electrode that corresponds to the adjacent filter is stimulated using one of the stimulation signal. Preferably, the adjacent filter is more basal and at a lower frequency than the selected filter. Note that the stimulation is applied using electrodes or a technique that focuses the stimulation signal to a discrete stimulation site, such that a broad recruitment of neighboring nerves does not occur. Next in block 514 the time delay cancels stimulation from the electrodes. Once completed, the electrode that corresponds to the selected filter is stimulated using the other stimulation signal in block 516. In some embodiments the stimulation site corresponding to the selected filter may be stimulated first in block 512, followed by the time delay in block 514 and then stimulation using the adjacent filter in block 514. These stimulation patterns may be repeated as shown by process arrow 518 as determined by the strategy. Once the stimulation is completed the sound processor takes the next sound signal in block 520.

Embodiments that use such a method may provide stimulation that allows the sound processor to elicit a strong musical pitch percept. The CNS extracts musical pitch from auditory nerve discharges primarily by a) identifying sites of localized phase discontinuity (i.e. harmonics); and b) assessing the spacing along the basilar membrane between adjacent harmonics, such that large spacing indicates a low fundamental and vice versa. These methods take advantage of place theory with a temporal metric, such as a local phase discontinuity, as a measure of activity rather than nerve discharge rate.

Figure 6:
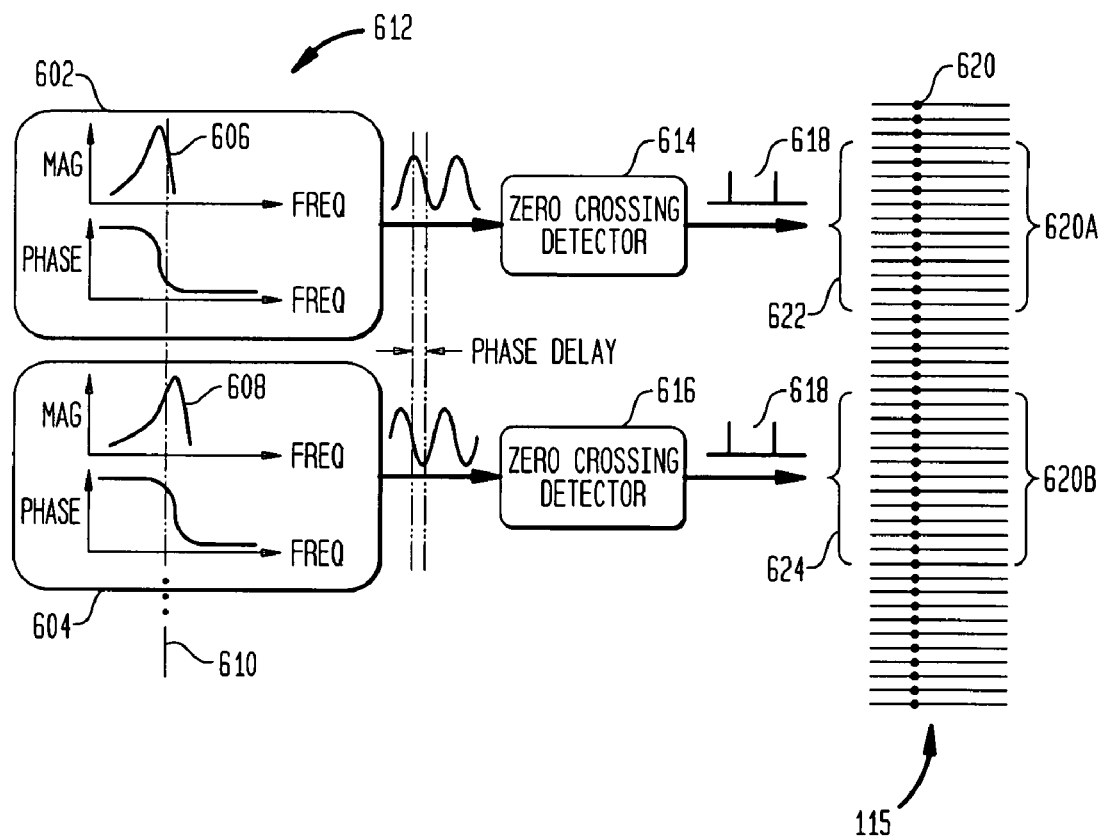
FIG. 6 is a block diagram of two adjacent filters implementing embodiments of the present invention.

One exemplary embodiment that uses two adjacent filters 602, 604 exhibiting a magnitude 606, 608 from a received sound signal in the vicinity of a single frequency component 610 is illustrated in FIG. 6. Adjacent filters 602, 604 are part of a filter bank 612, consisting of several other filters (not shown). It is understood that additional filters would span the entire audio frequency range of humans. The frequency component selector (not shown) selects the magnitude 606 of filter 602 for representation and also selects adjacent filter 604. Magnitudes 606, 608 are selected since filter 602, 604 exhibits a localized phase discontinuity near the frequency component 610. The localized phase discontinuity indicates from the phase response indicates that the filter contains the frequency components sufficient to convey pitch information to the recipient. Frequency component 610 is a tone frequency, i.e. a frequency that is most closely associated with pitch. Next a time instant is determined using zero crossing detectors 614, 616 based on at least the filter outputs. This delay is inserted between the pulses 618 generated using a compression function (not shown). Pulses 618 stimulate nerve populations 620 using two discrete electrodes 622, 624. Note that stimulation from electrode 622 stimulates only nerve population 620A, while stimulation from electrode stimulates only nerve population 620B. The stimulation is repeated, separated by time instant, to convey pitch perception information to the recipient. Multiple frequency components, such as those that are used to convey the sound, could also be processed rather than just the single component illustrated in FIG. 6.

Although the adjacent filters 602, 604 are shown throughout the figures as being next to each other, filters 602, 604 may also be adjacent even if not immediately next to each other. Thus, an adjacent filter may be separated by one or more filters from the selected filter. Preferably, the adjacent filter is stimulated first with the stimulation signal.

In this embodiment analyzing the incoming sound signal and determining the time instant are accomplished by the filters themselves. Selecting the components to be represented may be accomplished implicitly by the compression function relating filter output magnitude to stimulus magnitude. Compression curves are usually constructed with a "dead band" such that filters with weak outputs are ignored, thus "deselecting" some places for stimulation. If the compression function does not have a "dead band" there is no explicit deselection. Instead, all components are represented, but weak components result in weak stimulation signals. Selecting the stimulation site is accomplished by coupling stimulation signal generated from appropriate filters to appropriate channels of stimulation.

Figure 7:
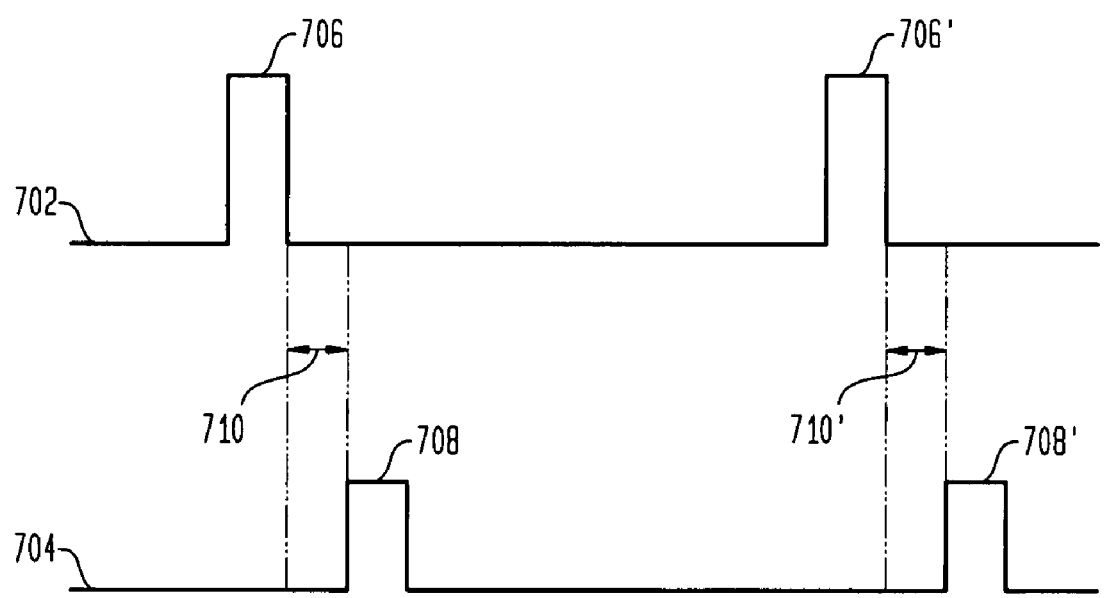
FIG. 7 is a timing diagram of pulses on the two channels illustrated in FIG. 6.

FIG. 7 is a pulse timing diagram of two adjacent channels 702, 704 each having a pulse 706, 708. Pulse 706 is separated by pulse 708 by time instant 710. Pulse 706' is separated by pulse 708' by time instant 710'. Note that time instant 710 and 710' may be the same value in some embodiments. The time between pulse 708 and 706' may depend on the tuning of the two filters from which the pulses are generated. In other embodiments the time between pulse 708 and 706' may be a fixed delay that is set in advance.

In an alternative embodiment, in place of the filter bank shown, the incoming sound signal may be analyzed with a Fast Fourier Transform (FFT) to determine the frequency components of the sound signal. The FFT is a well known mathematical algorithm that is used for analysis of digitally represented signals. The FFT determines amount of energy in each of N uniformly space frequency ranges (bins) where N is determined by the number of samples in the input signal. The frequency bins are distributed between 0 Hz (DC) and $F_{samp}/2$ where $F_{samp}$ is the rate at which the signal has been sampled.

In this alternative embodiment analyzing the sound signal and determining which components to represent would be accomplished by examination of the output of the FFT. Components to be represented would be determined by selecting frequency bins, or groups of adjacent bins, containing high energy. The corresponding stimulation sites would then be stimulated with an appropriate time delay. Harmonic complexes could be identified by additional analysis of the Fourier transform output, e.g. by autocorrelation of the magnitude spectrum to identify components at multiples of a fundamental frequency.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for representing a sound signal for a prosthetic hearing implant comprising:
   receiving a sound signal;
   obtaining a plurality of frequency components from the received sound signal;
   selecting a frequency component from amongst the plurality of frequency components;
   determining, based on the selected frequency component, a second channel adjacent to a first channel, wherein the first channel corresponds to the selected frequency component, and wherein the first channel corresponds to a first stimulation site and the second channel corresponds to a second stimulation site;
   generating a stimulation signal based on the selected frequency component; and
   determining a time delay between when stimulation is to be applied at the second stimulation site and when the first stimulation site is independently stimulated with the stimulation signal.

2. The method of claim 1, further comprising:
   stimulating the second stimulation site with the stimulation signal;
   delaying stimulation of the first stimulation site with the time delay; and
   stimulating the first stimulation site with the stimulation signal.

3. The method of claim 2, further comprising repeating:
   stimulating the second stimulation site with the stimulation signal;
   delaying stimulation of the first stimulation site with the time delay; and
   stimulating the first stimulation site with the stimulation signal.

4. The method of claim 1, wherein the first stimulation site and second stimulation site each comprise a discrete population of nerve fibers in a cochlea.

5. The method of claim 1, wherein obtaining a plurality of frequency components from the received sound signal comprises:
   filtering the received sound signal using a filter bank to obtain the plurality of frequency components; and
   wherein selecting at least one of the plurality of frequency components comprises selecting the frequency component with the largest magnitude from the plurality of frequency components.

6. The method of claim 1, wherein obtaining a plurality of frequency components from the received sound signal comprises:
   filtering the received sound signal using a filter bank to obtain the plurality of frequency components; and
   wherein selecting the frequency component comprises selecting a frequency component based on whether a filter of the filter bank corresponding to the frequency component exhibits a localized phase discontinuity near a tone frequency.

7. The method of claim 6, wherein the tone frequency is determined by a normal hearing model applied to the sound signal.

8. The method of claim 1, wherein the stimulation of the first stimulation site is independent of the stimulation of the second stimulation site.

9. The method of claim 1, wherein obtaining a plurality of frequency components from the received sound signal comprises:
   filtering the sound signal using a plurality of filters to determine frequency components for each filter of the plurality of filters.

10. The method of claim 9, wherein each filter of the plurality of filters is a minimum-phase linear filter.

11. The method of claim 1, wherein the second stimulation site is a location in the cochlea that is more basal than the first stimulation site.

12. The method of claim 1, wherein the time delay is based on at least detecting a positive peak of the selected frequency component.

13. The method of claim 1, wherein the time delay is based on at least detecting a zero-crossing of the selected frequency component.

14. The method of claim 1, further comprising the step of:
   stimulating the first stimulation site and the second stimulation site with one or more electrodes on an electrode array.

15. A sound processor for a prosthetic hearing implant comprising:
   a plurality of filters that each produce an output from a sound signal;
   a frequency selector configured to select the output from a selected filter of the plurality filters and, based on the selected filter, select an adjacent filter of the plurality of filters that is adjacent to the selected filter; and
   a timing delay generator configured to determine a time delay that separates a first stimulation signal from another filter and a second stimulation signal from the selected filter.

16. The sound processor of claim 15, further comprising:
   a microphone configured to convert the sound signal into an electrical signal;
   a preamplifier configured to control the level of the electrical signal; and
   an A/D converter configured to produce a digital output of the electrical signal.

17. The sound processor of claim 15, further comprising:
   an encoder configured to transmit the first stimulation signal, the time delay, and the second stimulation signal to an internal receiver unit.

18. The sound processor of claim 17, wherein the internal receiver unit is connected to a plurality of electrodes that discretely stimulate two stimulation sites within a cochlea using the first stimulation signal, and the second stimulation signal.

19. The sound processor of claim 15, wherein the frequency selector further comprises:
   means for selecting the filter having the output with the largest magnitude.

20. The sound processor of claim 15, wherein the selected filter exhibits a localized phase discontinuity that is near a tone frequency.

21. The sound processor of claim 20, wherein the tone frequency is determined by a normal hearing model applied to the sound signal.

22. The sound processor of claim 15, wherein each of the filters is a minimum-phase linear filter.

23. A system for representing a sound signal for a prosthetic hearing implant comprising:
   means for receiving a sound signal;
   means for obtaining a plurality of frequency components from the received sound signal;
   means for selecting a frequency component from amongst the plurality of frequency components;
   means for determining, based on the selected frequency component, a second channel adjacent to a first channel, wherein the first channel corresponds to the selected frequency component, and wherein the first channel corresponds to a first stimulation site and the second channel corresponds to a second stimulation site;
   means for generating a stimulation signal based on the selected frequency component; and
   means for determining a time delay between when stimulation is to be applied at the second stimulation site and when the first stimulation site is to be independently stimulated with the stimulation signal.

* * * * *